United States Patent [19]

Holtkamp, Sr.

[11] Patent Number: Plant 6,432

[45] Date of Patent: Nov. 29, 1988

[54] AFRICAN VIOLET PLANT NAMED MARILYN

[76] Inventor: Reinhold Holtkamp, Sr., Werther Strasse 112, D4294 Isselburg, Fed. Rep. of Germany

[21] Appl. No.: 21,787

[22] Filed: Mar. 4, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of African violet named Marilyn characterized by its large, single, mainly white flowers with purple centers and occasional purple tinging on the edges; pink in the centers; strong, upright flower stems that curve toward the center to form a bouquet above the leaves; profuse flowering, vigorous growth habit, flowering 9–10 weeks after potting, and its long-lasting and non-dropping flowers.

1 Drawing Sheet

The present invention comprises a new and distinct cultivar of African violet plant, botanically known as *Saintpaulia ionantha,* and hereinafter referred to by the cultivar name Marilyn.

The new cultivar was referred to during the breeding and selection process by the designation G 9/X, and is a product of a planned breeding program. The new cultivar was originated from a cross made by me in the controlled breeding program in Isselburg, Federal Republic of Germany. The female, or seed parent, was a cultivar designated D 150/2 Red Girl. The male, or pollen parent, was a cultivar designated D 134/11 Lilac Frilled.

Marilyn was discovered and selected by me in 1980 as a flowering plant within the progeny of the stated cross in a controlled environment in Isselburg, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Marilyn has not been observed under all possible environmental conditions. The phenotype may vary significantly with variations in environment such as temperature, light intensity and day length. The following observations, measurements and values describe the new cultivar as grown in Haffen, Federal Republic of Germany, and Nashville, Tenn., under greenhouse conditions which closely approximate those generally used in commercial practice.

The following traits have been repeatedly observed and are determined to be basic characteristics of Marilyn, which in combination, distinguish this African violet as a new and distinct cultivar:

(1) Strong, upright flower stems curving slightly toward the center.

(2) The single white flowers have a tiny touch of very light purple in the center and occasionally a trace of the same color on parts of some edges.

(3) First flash of flowers form a tight bouquet above the leaves.

(4) Profuse flowering.

(5) Each plant carries 8–10 upright flower stems each of which carries 10–12 flowers.

(6) Vigorous grower.

(7) Plant saleable 9–10 weeks after potting.

(8) Medium green, velvety and shiny leaves, hairy.

(9) Long-lasting, non-dropping single flowers.

(10) Seed capsules push slightly through.

(11) After maturity the flowers dry off and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Color Chart (R.H.S.), except where general colors of ordinary significance are referred to. Color values were taken under natural sunlight conditions at approximately 2:00 p.m. in Nashville, Tenn.

Botanical classification: *Saintpaulia ionantha,* Ramat., cv. Marilyn.

Parentage:

*Male parent.*—D 134/11 Lilac Frilled.

*Female parent.*—D 150/2 Red Girl.

Propagation: The new cultivar holds its distinguishing characteristics through successive propagations by leaf cuttings.

Plant: From 10 cm to 11 cm tall when grown in pots, and approximately 27–29 cm in diameter when fully grown.

*Leaves.*—General form: Oval to heart-shaped. Diameter: 60–75 mm. Texture: Velvety. Aspect: Hairy, shiny, serrated. Veins: Upperside: visible; underside: well pronounced, light green, shiny. Color (upper side): Green Group 137A. Color (under side): Yellow Green Group 148D and lighter. Petiole: Strong, upright, light green, hairy.

Flowers.—Buds: Bell-shaped, 7–9 mm before opening. Sepals: Five (5). Calyx: Shape: Funnel-shaped. Aspect: Spear-shaped, hairy. Peduncle: Character: Strong, upright, hairy. Color: Green, sometimes with purplish tinge.

Individual flowers: Size: 40–45 mm. Shape: Single, violet shaped, frilled edges. Color (upper side): White, with 82B in center and occasionally on edges. The edge tinging does not appear in the color photograph. Color (under side): White with a touch of 82D. Borne: Each flower stem carries 10–12 flowers on strong, upright, wirelike peduncles with flowers standing above the leaves. Flowering habit: Flowers 9–10 after potting.

*Reproductive organs.*—Stamens: 2. Anthers: 2, composed of 4 anther cells. Filaments: Yellowish green, 4 mm long. Pollen Color: Yellow Group 7A. Styles: 8 mm long, pink; base of ovary light green.

*Roots.*—Normally developed, white when young, turning slightly brownish when older.

Disease resistance: Good.

General observations: Marilyn is a vigorous and floriferous grower, with attractive velvety, medium green serrated leaves. Out of the center, 8–10 strong flower stems appear that are slightly bent toward the center, each carrying 10–12 single flowers with frilled edges. The blossoms are plain white with purple centers. Purple tinging also occasionally appears on the edges of the 2 smaller petals, the purple being approximately 4 mm wide, and on the 3 larger petals, where the purple edge can become as small as a line. The fully developed flower head forms a tight bouquet. Approximately 9–10 weeks after potting the plant is saleable. The flowers are long-lasting and non-dropping and the seed capsule pushes slightly through. Marilyn is a semperflorence.

I claim:

1. A new and distinct cultivar of African violet named Marilyn, characterized by its large, single, mainly white flowers with purple centers and occasional purple tinging on the edges; pink in the centers; strong, upright flower stems that curve toward the center to form a bouquet above the leaves; profuse flowering, vigorous growth habit, flowering 9–10 weeks after potting, and its long-lasting and non-dropping flowers.

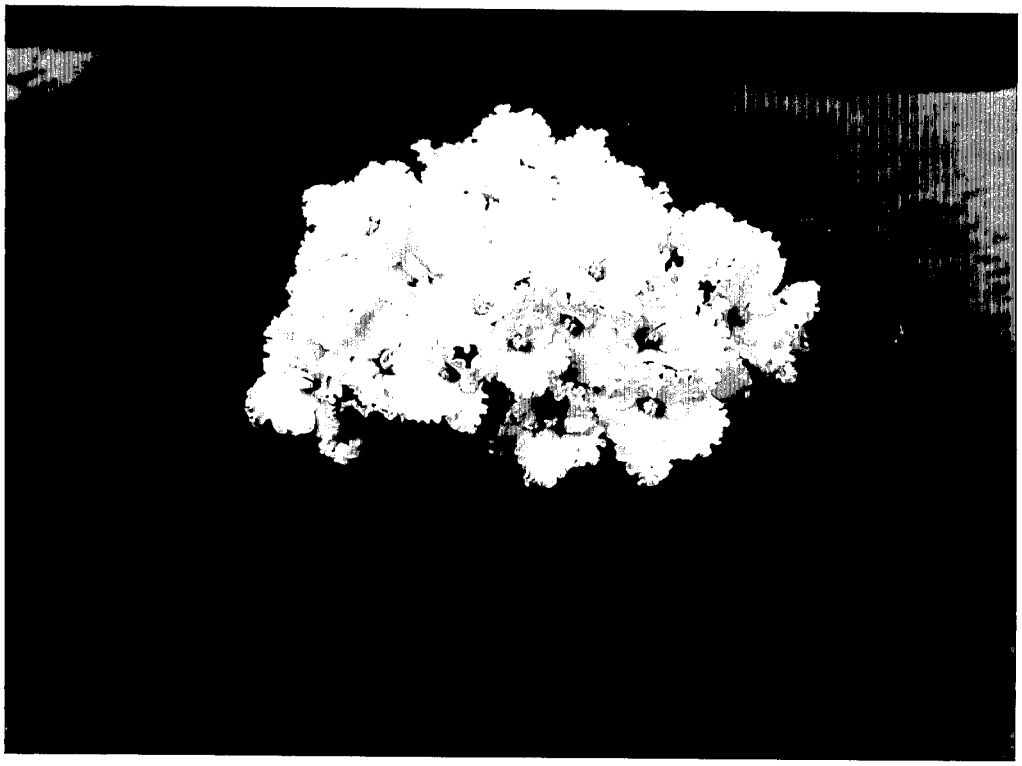

* * * * *